United States Patent [19]

Maruhashi et al.

[11] 4,436,663
[45] Mar. 13, 1984

[54] PROCESS FOR SEPARATING PORPHYRINS

[75] Inventors: Kenji Maruhashi, Yokohama; Ichiro Kojima, Yokosuka; Yutaka Oguchi; Noboru Endoh, both of Tokyo; Tetsuo Satoh, Yokohama, all of Japan

[73] Assignee: Nippon Oil Company, Ltd., Japan

[21] Appl. No.: 404,054

[22] Filed: Aug. 2, 1982

[30] Foreign Application Priority Data

Aug. 4, 1981 [JP] Japan ................... 56-121359

[51] Int. Cl.$^3$ ........................... C07D 487/22
[52] U.S. Cl. .................................. 260/245.91
[58] Field of Search ....................... 260/245.91

[56] References Cited

FOREIGN PATENT DOCUMENTS 54-41313  4/1979  Japan .
2030564   4/1980  United Kingdom .
2072670  10/1981  United Kingdom .

Primary Examiner—Richard Raymond
Attorney, Agent, or Firm—Wenderoth, Lind & Ponack

[57] ABSTRACT

A process for separating porphyrins, which comprises
(1) adjusting the pH of the liquid phase of a culture broth containing at least two porphyrins to about 2.5 to about 4 and collecting the resulting solid containing the porphyrins,
(2) either (a) preparing an acidic aqueous solution of said solid and adjusting the pH of its liquid phase left after removal of insoluble matter to about 6 to about 8 to form an aqueous solution containing the porphyrins, or (b) preparing an acid-containing lower alcohol solution of said solid, adjusting the pH of its liquid phase left after removal of insoluble matter, adding water in an amount at least twice the amount of the solution to precipitate lower alkyl esters of the porphyrins, collecting the precipitates and dissolving them in an organic solvent to form an organic solvent solution of the porphyrin esters,
(3) contacting the solution obtained in (a) or (b) in step (2) with a copolymer having a surface area of at least about 700 m$^2$/g and derived from
  (i) divinylbenzene,
  (ii) styrene or its functional derivative,
  (iii) an alkenyl ester of a benzenepolycarboxylic acid represented by the following formula

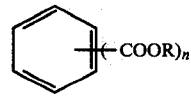

wherein R represents an alkenyl group having 3 to 10 carbon atoms, and n is 2 or 3, thereby permitting adsorption of the porphyrins or their esters to the copolymer, and (4) thereafter, eluting the copolymer to obtain fractions of the individual porphyrins or their esters; and an adsorbent for use in the above-mentioned process.

7 Claims, No Drawings

PROCESS FOR SEPARATING PORPHYRINS

This invention relates to a process for separating porphyrins of high purity in high yields in the form of free carboxylic acids or their lower alkyl esters from a culture broth containing at least two kinds of porphyrin. According to this process, porphyrins of high purity can be recovered at very high ratios of, for example, more than 90% with good selectivity by a simple and easy adsorption-elution operation in a simple apparatus at satisfactory fast rates of adsorption and elution. Furthermore, the adsorbent used in the process has excellent durability in repeated use.

The invention also relates to a polymeric adsorbent suitable for use in the practice of the above-mentioned process.

Porphyrins, occurring widely in the tissues of various organisms, are biologically active compounds which are important as constituents of heme protein which has to do with physiological actions such as transport of oxygen within the organisms and catalytic action on oxidation-reduction reactions within the organisms. They are active substances which in medical applications, show interesting physiological activity in regulating various organs of the body, for example in improving the function of the liver.

Generally, porphyrins are produced by extraction from hemoglobin in the blood or by cultivation of microorganisms having the ability to produce porphyrins. It is not always easy to isolate the porphyrins with good efficiency from co-existing other components of the tissues. Sometimes, two or more kinds of porphyrin are produced together. It is desired therefore to develop an industrial method capable of separating and recovering them efficienctly.

Some methods have been known in the past for separating and recovering porphyrin. They include, for example, a method which comprises collecting porphyrins using a solvent such as acetic acid-ethyl acetate, converting the extracted porphyrins to their methyl ester, and subjecting them to an adsorbent chromatographic procedure using an adsorbent such as alumina [J. Chromatog., 5 (1961) 277–299; Bichem. J., 62 (1956) 78], and a method which comprises dissolving a culture broth containing porphyrins in an aromatic hydrocarbon, boiling the solution, and then cooling it to precipitate crystals (Japanese Patent Publication No. 37042/1977).

These prior methods have proved to be unsuitable for industrial practice from the standpoint of separating efficiency, operations, etc. when applied to the separation of porphyrins from a mixture containing two or more kinds of porphyrins.

A method which comprises purifying porphyrins in the form of a free acid using an anion exchange resin was suggested [Journal of the Agricultural Chemical Society of Japan, 50, 41–47 (1976)]. This method is not industrially advantageous, however, because the ratio of recovering porphyrins is low.

The present inventors made investigations in order to develop a process for separating porphyrins which is free from the aforesaid defects of the prior methods. These investigations have led to the discovery that purified porphyrins of high purity can be separated and recovered in high yields with good selectivity in recovery ratios of, for example, more than 90% by a process which comprises (1) adjusting the pH of the liquid phase of a culture broth containing at least two porphyrins to about 2.5 to about 4 and collecting the resulting solid containing the porphyrins, (2) either (a) preparing an acidic aqueous solution of said solid and adjusting the pH of its liquid phase left after removal of insoluble matter to about 6 to about 8 to form an aqueous solution containing the porphyrins, or (b) preparing an acid-containing lower alcohol solution of said solid, adjusting the pH of its liquid phase left after removal of insoluble matter, adding water in an amount at least twice the amount of the solution to precipitate lower alkyl esters of the porhyrins, collecting the precipitates and dissolving them in an organic solvent to form an organic solvent solution of the porphyrin esters, (3) contacting the solution obtained in (a) or (b) in step (2) with a copolymer having a surface area of at least about 700 m$^2$/g and derived from
   (i) divinylbenzene,
   (ii) styrene or its functional derivative, and
   (iii) an alkenyl ester of a benzenepolycarboxylic acid represented by the following formula

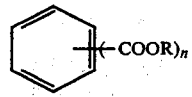

wherein R represents an alkenyl group having 3 to 10 carbon atoms, and n is 2 or 3,
thereby permitting adsorption of the porphyrins or their esters to the copolymer, and (4) thereafter, eluting the copolymer to obtain fractions of the individual porphyrins or their esters.

It has also been found that the above process can be performed at satisfactory fast rates of adsorption and elution, and the resin adsorbent used for porphyrin separation has excellent durability even in repeated use.

Investigations of the present inventors have shown that porphyrin-producing microorganisms such as *Arthrobacter hyalinus* (FERM-P No. 3125; ATCC 31263; DSM-867) and *Arthrobacter pascens* (ATCC 13346; IFO 12139) and their mutants or variants have the ability to form a culture broth containing 2 to 5 porphyrins in the form of free acids containing 4, 5, 6, 7 and 8 carboxyl groups respectively; and that the copolymer specified in (3) above has the excellent ability to adsorb selectively these carboxy-containing porphyrins or their lower alkyl esters in the solution formed by steps (1) and (2) above in large amounts, and in eluting the copolymer, the purity of the porphyrins in active fractions is sufficiently high, thus showing selective eluting ability and a high level of porphyrin separating ability. It has been found that pure porphyrins can be separated and recovered in a high recovery ratio of more than 90% by a simple and easy operation of adsorption and elution in a simple apparatus without requiring additional after-purifying means and/or preliminary purifying means.

It has further been found that the copolymer used in step (3) shows satisfactory rates of adosrbing and eluting the carboxy-containing coproporphyrins or their esters in the solution obtained by steps (1) and (2), and is free from blockage even in repeated operations and shows excellent durability, and that the copolymer permits advantageous industrial purification and separation of porphyrins from a solid containing porphyrins and foreign materials which is collected from the culture broth.

It is an object of this invention to provide a process for separating porphyrins from a culture broth containing at least two kinds of porphyrins, making it possible to obtain the individual porphyrins in high purity.

Another object of this invention is to provide an adsorbent for separating porphyrins which is suitable for the practice of the aforesaid process.

The above and other objects and advantages of this invention will become apparent from the following description.

The culture broth containing porphyrins which is to be subjected to separating treatment in accordance with the process of this invention may be any culture broth which contains at least two kinds of porphyrin. In the present invention, the porphyrins are meant to include uroporphyrins I to IV, coproporphyrins I to IV, and their partially esterified products and their partially decarboxylated products. There can be used a culture broth containing at least two kinds of porphyrin having 4 to 8 carboxyl groups in the side chain.

Many porphyrin-producing microorganisms for forming a culture broth containing at least two porphyrins are known. For example, the known porphyrin-producing microorganisms described in Japanese Laid-Open Patent Publications Nos. 7479/1977, 109929/1978 (corresponding to German OLS No. 2809093), 68398/1981 (corresponding to British Patent Publication No. 2066834) and 78595/1981 (corresponding to British Patent Publication No. 2077284).

Among these microorganisms, porphyrin-producing strains of the genus Arthrobacter are preferred because culture broths formed by cultivating these strains contain two or more porphyrins in high concentrations.

Examples of these preferred known porphyrin-producing strains include *Arthrobacter hyalinus* (FERM-P No. 3125; ATCC 31263; DSM-867) and *Arthrobacter pascens* (ATCC 13346; IFO 12139) disclosed in the above-cited patent documents and their mutants or variants, such as a 5-methyl-DL-tryptophan resistant strain (FERM-P No. 5256, ATCC 31736, DSM 1932) of *Arthrobacter hyalinus* (a coproporphyrin III resistant strain (FERM-P No. 5259, ATCC 31739, DSM-1933) of *Arthrobacter hyalinus*, and an L-tryptophan resistant strain (FERM-P No. 5257, ATCC 31737, DSM-1934) of *Arthrobacter pascens.*

Other examples of known porphyrin-producing strains are *Arthrobacter cremeus* (FERM-P No. 3126), *Arthrobacter resinosus* (FERM-P No. 3131), *Arthrobacter isopropanolophila* (FERM-P No. 3129), *Arthrobacter flavidus* (FERM-P No. 3130), *Brevibacterium eburneus* (FERM-P No. 3128), and *Brevibacterium lacticolor* (FERM-P No. 3127). The microbiological characteristics of these porphyrin-producing strains are described in detail, for example in the above-cited patent documents.

In the above list of microorganisms, ATCC stands for American Type Culture Collection, U.S.A.; FERM, Fermentation Research Institute, Agency of Industrial Science and Technology, Japan; DSM, German Collection of Microorganisms, Germany; and IFO, Institute of Fermentation, Osaka, Japan.

The above-cited patent documents also describe in detail techniques of forming porphyrin-containing culture broths by cultivating the above-exemplified porphyrin-producing strains, the cultivating conditions, etc. which can be utilized in the formation of the starting culture broth in this invention. The formation of the starting culture broth will be described below briefly.

Cultivation for the formation of the broth can be effected, for example, in a culture medium containing suitable carbon, nitrogen and mineral sources under suitable cultivating conditions including optimal pH and temperature conditions known with regard to the above-exemplified known strains.

For example, a starting broth especially suitable for the practice of the process of this invention which contains fice kinds of porphyrin (a mixture of porphyrins containing 4, 5, 6, 7 and 8 carboxyl groups respectively) may be obtained by cultivating a porphyrin-producing strain of the genus Arthrobacter, preferably *Arthrobacter hyalinus, Arthrobacter pascens* or a mutant or variant thereof at a temperature of about 20 to about 40° C. and a pH of about 4 to about 9.5. The cultivating time can be properly selected, and for example, it is about 2 to 20 days.

Examples of suitable nitrogen sources are corn steep liquor, yeast extract, meat extract, peptone, amino acids, hyrolyzed proteins, fish meal, ammonium salts, nitric acid salts and urea. They may be used in a combination of two or more. Examples of suitable carbon sources are carbohydrates, alcohols, hydrocarbons, and bran. They can also be used in a combination of two or more. Examples of mineral sources are phsophoric acid salts, magnesium salts, zinc salts, calcium salts, manganese salts, molybdenum salts and copper salts. They may be used in a combination of two or more.

According to the process of this invention, a culture broth containing at least two porphyrins, preferably a mixture of at least two of porphyrins in free acid from containing 4, 5, 6, 7 and 8 carboxyl groups respectively, is used as a starting material. The liquid phase of this broth is adjusted to pH about 2.5 to about 4, preferably about 2.8 to about 3.8, and the resulting solid containing the porphyrins is collected [step (1)].

The pH adjustment of the liquid phase gives a solid containing at least two porphyrins. Usually, the solid is formed as a precipitate, and can be collected by any desired solid-liquid separating means such as decantation, centrifugal separation and filtration.

Examples of acidic substances which can be used for pH adjustment in step (1) include inorganic acids such as sulfuric acid, hydrochloric acid, nitric acid and phosphoric acid and organic acids such as formic acid, acetic acid, oxalic acid and lactic acid.

The porphyrin-containing solid which can be collected as above can be obtained as a solid material composed of at least two porphyrins which have been fairly well separated selectively from carbon, nitrogen and mineral sources and other impurities which can be included in the liquid phase.

In step (2) of the process of this invention, the resulting porphyrin-containing solid is then subjected to the procedure (a) or (b) below to form an aqueous solution containing the porphyrins, or an organic solvent solution containing the lower alkyl esters of the porphyrins.

(a) A procedure which comprises preparing an acidic aqueous solution of the solid and adjusting the pH of its liquid phase left after removal of insoluble matter to about 6 to about 8.

(b) A procedure which comprises preparing an acid-containing lower alcohol solution of the solid, adjusting the pH of its liquid phase left after removal of insoluble matter, adding water in an amount at least twice the amount of the solution to precipitate lower alkyl esters of the porphyrins, collecting the precipitates and dissolving them in an organic solvent.

In the procedure (a), an acidic aqueous solution of the resulting porphyrin-containing solid is prepared, and the liquid phase left after removal of insoluble matter is adjusted to pH about 6 to about 8, preferably to about 7±0.5. The acidic aqueous solution can be prepared by redissolving the porphyrin-containing solid obtained in step (1) in an acidic aqueous solution. Examples of useful acids include inorganic acids such as hydrochloric acid, sulfuric acid, nitric acid and phosphoric acid and organic acids such as formic acid, acetic acid, oxalic acid and lactic acid. The concentration of the acid is, for example, about 1 to about 4 N, preferably about 2 N.

Removal of insoluble matter from the pH-adjusted acidic aqueous solution containing the porphyrins can be performed by utilizing any desired solid-liquid separating means such as decantation, centrifugal separation and filtration. The pH of the solution obtained by removing the insoluble matter in the above manner can be adjusted to about 6 l to about 8 by using a suitable alkaline substance. Examples of the alkaline substance used for this pH adjustment include sodium hydroxide, potassium hydroxide, aqueous ammonia, sodium carbonate, and potassium carbonate.

According to the procedure (b), an acid-containing lower alcohol solution of the porphyrin-containing solid is prepared and left to stand usually for 1 to 12 hours to induce esterification, and the pH of the liquid phase left after removal of the resulting insoluble matter is adjusted to about 6 to about 8, preferably about 7±0.5. This operation can be performed in the same way as in the procedure (a) except that an acid-containing lower alcohol is used instead of the acid aqueous solution used in the procedure (b), water is added in an amount at least about twice the amount of the alcohol solution, and there are used such temperatures and time periods which are sufficient to form the lower alkyl esters of the porphyrins. Examples of the acid used are inorganic acids, such as hydrochloric acid, sulfuric acid, nitric acid and phosphoric acid and organic acids such as formic acid, acetic acid, oxalic acid and lactic acid. The concentration of the acid in the solution is, for example, 5 to 15%. The amount of water to be added is, for example, about 2 to about 20 times the amount of the acid-containing lower alcohol solution. Esterification does not particularly require heating, and the same conditions as in procedure (a) can be used. For example, it may be carried out at a temperature of about 0° to about 30° C. for a period of about 1 to about 24 hours. These specific temperature and time conditions also apply to the procedure (a).

Since in the procedure (b), the lower alkyl esters of the porphyrins are precipitated in the presence of water added, an organic acid solution of the lower alkyl esters of the porphyrins can be prepared by collecting the precipitates and dissolving them in an organic solvent. Collection of the precipitates can be performed by using the same solid-liquid separating means as described hereinabove.

Examples of the lower alcohol used in the procedure (b) are methanol, ethanol, propanol and butanol. Examples of the organic solvent used to re-dissolve the precipitates include chlorine-containing solvents such as dichloromethane, chloroform and carbon tetrachloride. A methanol/chloroform mixed solvent, particularly a 2:3 by volume mixture of methanol and chloroform, is preferred. Preferred solvents are, for example, a methanol/chloroform mixed solvent, preferably a 2:3 by volume mixture of methanol and chloroform.

In step (3) of the process of this invention, the solution prepared in (a) or (b) of step (2) is contacted with a copolymer (to be sometimes referred to as DST resin hereinafter) having a surface area of at least about 700 m²/g and derived from (I) divinylbenzene.
(ii) styrene or its functional derivative, and
(iii) an alkenyl ester of a benzenepolycarboxylic acid represented by the following formula

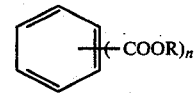

wherein R represents an alkenyl group having 3 to 10 carbon atoms, and n is 2 or 3,
thereby causing adsorption of the porphyrins or their esters to the resin.

Step (3) may be carried out by any means which can effect sufficient contact of the solution prepared in (a) or (b) with the DST resin adsorbent having a surface area of at least about 700 m²/g. For example, there can be used a batch method which comprises mixing the adsorbent and thw porphyrin-containing solution and if desired stirring the mixture for contact. A column chromatographic method can also be used which comprises filling the adsorbent into a suitable column, and passing the porphyrin-containing solution through the column.

According to step (4) of the process of this invention, the DST resin having a surface area of at least about 700 m²/g and having the porphyrins or their esters adsorbed thereto is then eluted with an eluent to separate at least two porphyrins contained in the liquid phase of the starting broth into fractions containing the individual porphyrins. Thus, the individual porphyrins of high purity can be obtained in high yields.

When the aqueous solution containing the porphyrins prepared by the procedure (a) is to be subjected to adsorption in step (3), the pH employed is about 6 to about 8. When the organic solvent solution containing the esters of the porphyrins obtained by the procedure (b) is to be adsorbed, a batch method may be employed which comprises mixing the adsorbent with the solution and as required, stirring the mixture for contact. Or there can be used a column-chromatographic method which comprisses filling the adsorbent into a suitable column, and passing the above solution of the porphyrin esters through the adsorbent layer. The adsorption treatment may be carried out at room temperature. No heating or cooling is particularly required. For example, temperatures of about 0° to about 30° C. may be employed in the adsorption treatment.

In the elution treatment in step (4), an aqueous solution of a lower alcohol is preferably used as an eluent when the porphyrin-containing aqueous solution prepared by the procedure (a) is used in step (3). An aqueous solution of a lower alcohol in a concentration of about 10 to about 40% is preferred. Suitably, it is used as an aqueous solution of a lower alcohol having a pH of about 7 to about 12. Examples of the lower alcohol are methanol, ethanol and isopropanol. For adjustment of the pH, an alkaline substance such as sodium hydroxide, potassium hydroxide, ammonia, and calcium hydroxide may be used.

If the organic solvent solution containing the esters of the porphyrins is used in step (3), a mixture of a lower alcohol and a chlorine-containing solvent such as dichloromethane, carbon tetrachloride and chloroform is a preferred eluent. Examples of the lower alcohol are methanol, ethanol, propanol and butanol. A mixture of the lower alcohol and the chlorine-containing solvent in a ratio of from 2:3 to 1:1 is especially preferred.

The elution treatment in step (4) may be carried out at room temperature, and no heating or cooling is particularly required. For example, the elution can be carried out at about 10° to about 60° C.

The porphyrin fractions are precipitated as solid porphyrin fractions by adjusting the pH to about 2.5 to about 4, and can be collected as solids.

One example of the elution pattern of the porphyrins and impurities in step (4) is as follows: By an eluting operation using an eluent, the impurities are first eluted, and then porphyrin having 8 carboxyl groups is eluted. Thereafter, porphyrin having 7 carboxyl groups comes out, and porphyrins having 6, 5, 4 . . . carboxyl groups follow in the order of decreasing number of carboxyl groups. The other foreign materials remain adsorbed to the column.

According to the process of this invention, the individual porphyrin fractions of high purity can be separated from the liquid phase of a culture broth containing at least two porphyrins in high yields by an easy operation and in a simple apparatus with excellent selectivity and at high recovery ratios.

The present invention also relates to a resin adsorbent for separation of porphyrins which is suitable for the practice of the process of this invention. This adsorbent can be widely used with outstanding separating ability for separating porphyrins from an aqueous solution containing at least two porphyrins or an organic solvent solution containing lower alkyl esters of the porphyrins, including porphyrin-containing aqueous solutions derived from the aforesaid culture broths.

An especially suitable adsorbent is an adsorbent for separation of porphyrins which is a copolymer having a surface area of at least 700 m²/g and derived from
 (i) divinylbenzene,
 (ii) styrene or its functional derivative, and
 (iii) an alkenyl ester of a benzenepolycarboxylic acid represented by the following formula

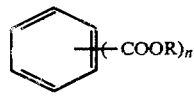

wherein R represents an alkenyl group having 3 to 10 carbon atoms, and n is 2 or 3,
the amount of the component (ii) being about 30 to about 80% by weight based on the total amount of the components (i) and (ii), and the amount of the component (iii) being about 0.1 to about 30% by weight based on the total amount of the components (i), (ii) and (iii), and said adsorbent being used for separating porphyrins or their esters from an aqueous solution or an organic solvent solution containing at least two porphyrins or their lower alkyl esters.

The DST resin used in the process of this invention has a moderately polar surface attributed to the alkenyl ester of the benzenepolycarboxylic acid of the formula

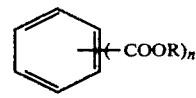

whereas styrene-divinylbenzene resins, such as Amberlite XAD resins (products of Rohm & Haas Co.) have no polar surface. It has better porphyrin-adsorbing ability than conventional resins as shown by the fact that the amount of porphyrins which the DST resin of this invention can adsorb is about 5 to 10 times as large as that adsorbed by the conventional resins. Furthermore, the DST resin shows excellent performance in selectivity during adsorption and elution, and permits fast rates of adsorption and elution, and excellent durability both before and after regeneration. Hence, it can exhibit outstanding properties as an adsorbent for separation of porphyrins.

The form of the adsorbent of this invention for separation of porphyrins may be freely chosen, and is, for example, powdery or granular. It should have a surface area of at least about 700 m²/g, preferably at least about 800 m²/g, for example about 700 to about 1,200 m²/g, preferably about 800 to about 1,200 m²/g.

In the present invention, the surface area of the adsorbent resin is measured and determined by the following method.

The resin is filled in a column, and a chloroform solution of each of 10 kinds of polystyrene having known molecular chain lengths and a chloroform solution of styrene are respectively passed through the resin-filled column. The volume of each polystyrene eluted is measured.

Each polystyrene has a molecular chain length of from $10^4$ Å to $10^2$ Å and the molecular chain length distribution is very narrow.

By using the molecular chain length (Å), the elution volume V (cc) and the amount of the resin, W (g), filled in the column, the surface area of the resin (S in m²/g) is obtained as follows:
 (1) $Vi\ (cc/g) = (Vm - Vn)/W$
 (2) $Si\ (m^2/g) = 8 \cdot Vi \cdot 10^4/(m+n)$
  $i = 8000$
 (3) $S\ (m^2/g) = \Sigma Si$
  $i = 15$
 Vi: the pore volume of mÅ ~ nÅ
 Vm: the volume of polystyrene of mÅ eluted
 Vn: the volume of polysturene of nÅ eluted
 Si: the surface area of mÅ ~ nÅ
 m and n: the molecular chain lengths If required, two or more styrene monomers (ii) and two or more alkenyl esters of the benzenepolycarboxylic acids may be used. Examples of the functional derivatives of styrene include those having a $C_1$-$C_6$ alkyl substituent, such as methylstyrene, ethylstyrene, dimethylstyrene and propylstyrene.

The amounts of the components (i) to (iii) can be properly selected. For example, the amount of the styrene component is about 30 to about 80% by weight, preferably about 45 to about 70% by weight, based on the total amount of divinylbenzene and styrene or its functional derivative, and the amount of the alkenyl ester of the benzene carboxylic acid is about 0.1 to about 30% by weight, preferably about 1 to about 10% by weight based on the total amount of divinylbenzene, the styrene component and the alkenyl ester. Divinylbenzene usually available commercially contains about 40 to about 70% by weight of m- and p-divinylbenzenes and about 30 to about 60% by weight of o-, m- and p-ethylstyrenes, and can therefore be used directly as the divinylbenzene and styrene components (i) and (ii).

Copolymerization of the aforesaid components (i), (ii) and (iii) may be carried out by known techniques. For example, the copolymer of this invention can be produced by copolymerizing divinylbenzene, styrene or its functional derivative and the alkenyl ester of benzenepolycarboxylic acid in suspension in an aqueous medium. Known radical polymerization initiators soluble in the above monomers may be used as polymerization initiators. Examples are benzyl peroxide, lauroyl peroxide, tert-butyl peracetate, tert-butyl perpivalate and azobisisobutyronitrile. The amount of the initiator can be properly chosen, and is, for example, about 0.1 to about 10% by weight, preferably about 0.5 to about 3% by weight.

The use of a dispersing agent is preferred in the suspension copolymerization in order to obtain a granular polymer. Examples of useful dispersing agents include difficulty-soluble salts such as barium sulfate, calcium carbonate and tricalcium phosphate, difficulty soluble inorganic compounds such as bentonite and clay, and natural and synthetic water-soluble polymers such as starch, methyl cellulose, gelatin, polyvinyl alcohol, partially saponified polyvinyl alcohol and polyacrylic acid salts. The amount of the dispersant can be properly chosen, and is, for example, about 0.1 to about 10% by weight, preferably about 0.5 to about 7% by weight, based on the monomeric mixture.

In addition to the dispersing agent, there can be used a dispersion stabilizer, for example various surface-active agents including sodium dodecylbenzenesulfonate. The use of the dispersing agent with or without the dispersion stabilizer prevents the solvent and the polymer components from partially coalescing with each other during the suspension polymerization to form a large gel, and makes it possible to produce a uniform copolymer composed of divinylbenzene, the styrene monomer and the alkenyl ester of benzenepolycarboxylic acid. Furthermore, the particle size distribution of the gel particles is improved, and an adsorbent resin having the excellent ability to separate porphyrins can be obtained.

In the suspension copolymerization using a large amount of water as a medium, a mixed solvent system may be used as desired which comprises a good solvent for at least one of divinylbenzene and the alkenyl ester of benzenepolycarboxylic acid. Examples of good solvents for divinylbenzene are alkylated benzenes such as diethylbenzene, trimethylbenzene and methylisopropylbenzene. Examples of good solvents for the alkenyl ester of benzenepolycarboxylic acid are aliphatic alcohols such as tert-isoamyl alcohol and tert-butyl alcohol. For example, when a mixture of tert-isoamyl alcohol and diethylbenzene is used as the solvent, it acts as a good solvent for one of the monomers and as a poor solvent for the other. Hence, such a solvent system serves to impart a macroreticular structure equally to the resulting resin particles, and to increase the porosity of the resin as a whole. Accordingly, it acts effectively to reduce the degree of swelling of the adsorbent resin of this invention and to impart better porphyrin-separating ability to the resin.

Preferably, the suspension copolymerization is generally carried out in an atmosphere of an inert gas such as nitrogen, and the polymerization temperature and time can be properly selected according to the type of the polymerization initiator, etc. For example, the copolymerization may be carried out at a temperature of about 0° to about 110° C., preferably about 50° to about 100° C. for about 5 to about 10 hours.

The following examples illustrate the separation and purification of porphyrins by the process of this invention using the adsorbent of this invention.

EXAMPLE 1

(1) A 150-liter stirred tank was charged with 5.0 kg of industrial-grade divinylbenzene (purity about 55%, the remainder being ethylvinylbenzene), 1 kg of tripropenyl 1,2,4-benzenetricarboxylate, 6.0 kg of diethylbenzene, 3 kg of isoamyl alcohol, 80 kg of benzoyl peroxide, 100 liters of water, 4 kg of tricalcium phosphate and 6 g of sodium dodecylbenzenesulfonate. With stirring, the aforesaid monomers were polymerized in suspension at 90° C. for 8 hours to give a granular crosslinked copolymer.

The resulting copolymer was filtered, washed with methanol and chloroform in a column, again filtered, and dried under reduced pressure at 60° to 80° C. to give 5.3 kg of a white opaque granular polymer.

The granules were calssified, and the properties of a divided portion having a particle size of 20 to 25μ were measured. It was found to have a surface area of 874 m²/g and a pore volume of 1.7 cc/g.

This resin showed an infrared absorption assigned to the carbonyl group at 1740 cm$^{-1}$. This demonstrates that tripropenyl 1,2,4-benzenetricarboxylate was effectively copolymerized and incorporated in the copolymer.

(2) *Arthrobacter hyalinus* (FERM-P No. 3125), a porphyrin-producing strain, was inoculated and cultivated at 30° C. for 3 days, in a 500 ml Erlenmeyer flask containing 250 ml of a sterilized culture medium containing the following ingredients.

Composition of the culture medium

Deionized water: 1 liter
iso-Propyl alcohol: 10 ml
Yeast extract: 1.0 g
Peptone: 3.0 g
Ammonium nitrate: 3.0 g
Monopotassium phosphate: 0.4 g
Disodium phosphate: 1.5 g
Magnesium sulfate: 5.0 g
Manganese sulfate: 10 ml
Zinc sulfate: 10 mg
Copper sulfate: 200 μg
Molybdenum trioxide: 10 μg
Calcium carbonate: 5.0 g
L-cystine: 0.2 g Thereafter, every 2 to 3 days, isopropyl alcohol was additionally supplied. The total amount of isopropyl alcohol added during a cultivation period of 17 days was 85 ml per liter of culture broth.

After the cultivation, the culture broth contained 260 mg/liter of porphyrin having 8 carboxyl groups, 80 mg/liter of porphyrin having 7 carboxyl groups, 30 mg/liter of porphyrin having 6 carboxyl groups, 21 mg/liter of porphyrin having 5 carboxyl groups, and 300 mg/liter of porphyrin having 4 carboxyl groups.

(3) One liter of the culture broth obtained as in (2) above was centrifuged at 10,000 G for 10 minutes to remove insoluble materials including the microbial cells. The pH of the resulting liquid phase was adjusted to 3.6, and the precipitate was separated by centrifugation at 1,000 G for 10 minutes. The precipitate obtained was dissolved in 500 ml of 2 N HCl. The solution was filtered to remove insoluble materials and adjusted to pH 7 with sodium hydroxide. The solution obtained was passed through a column filled with 3 liters of the resin particles obtained in (1) above at a rate of 200 ml per minute by a rising flow method to cause adsorption of the porphyrins. A 10% aqueous solution of methanol at a pH of 12 was passed continuously through the column to elute porphyrin having 8 carboxyl groups, porphyrin having 7 carboxyl groups, and porphyrin having 6 carboxyl groups in this order, and they were respectively collected as 400 ml fractions. Then, a 10% aqueous solution of methanol at a pH of 7 was passed through the column to elute porphyrin having 5 carboxyl groups and then porphyrin having 4 carboxyl groups. The former was collected as a 400 ml fraction, and the latter, as a 2 liter fraction. The fractions obtained were each adjusted to pH 3.2 with hydrochloric acid, and the precipitates were collected by filtration. The resulting porphyrin solids were 240 mg of porphyrin having 8 carboxyl groups, 71 mg of porphyrin having 7 carboxyl groups, 27 mg of porphyrin having 6 carboxyl groups, 19 mg of porphyrin having 5 carboxyl groups and 290 mg of porphyrin having 4 carboxyl groups which were recovered respectively at a recovery ratio of 92, 89, 90, 90, and 97%.

EXAMPLE 2

*Arthrobacter pascens* (IFO 12139), a porphyrin-producing strain, was cultivated in the same way as in Example 1 except that glucose was used instead of isopropyl alcohol. There was obtained a culture broth which contained 130 mg/liter of porphyrin having 8 carboxyl groups, 7.7 mg/liter of porphyrin having 7 carboxyl groups, 2.7 mg/liter of porphyrin having 6 carboxyl groups, 1.6 mg/liter of porphyrin having 5 carboxyl groups, and 70 mg/liter of porphyrin having 4 carboxyl groups. The culture broth was subjected to the same separating procedure as in Example 1, (3) and the above porphyrins were recovered at a ratio of 93, 91, 88, 87, and 94%, respectively.

EXAMPLE 3

The 5-methyl-DL-tryptophan resistant strain (FERM-P No. 5256) of *Arthrobacter hyalinus*, a porphyrin-producing strain, was cultivated in the same way as in Example 1, (2) to give a culture broth which contained 370 mg/liter of porphyrin having 8 carboxyl groups, 80 mg/liter of porphyrin having 7 carboxyl groups, 20 mg/liter of porphyrin having 6 carboxyl groups, 20 mg/liter of porphyrin having 5 carboxyl groups, and 220 mg/liter of porphyrin having 4 carboxyl groups.

One liter of the resulting culture broth was centrifuged at 10,000 G for 10 minutes to remove insoluble materials including the microbial cells. The pH of the resulting liquid phase was adjusted to 3.6, and the precipitate was separated by centrifugation at 1,000 G for 10 minutes. To the resulting precipitate was added 100 ml of 5% $H_2SO_4$-methanol and the mixture was left to stand overnight at 10° C. to convert the porphyrins to their methyl esters. The insoluble materials were separated by filtration, and the filtrate was put in 1 liter of water. The solution was adjusted to pH 7 with sodium hydroxide, and the resulting precipitate was collected by filtration.

The resulting solid was dissolved in a 3:2 mixture of methanol and chloroform, and the solution was passed through a column filled with 3 liters of the resin particles obtained in Example 1, (1) at a rate of 200 ml per minute by a rising flow method to cause adsorption of the porphyrin esters. A 3:2 mixture of methanol and chloroform was passed continuously through the column to elute a methyl ester of porphyrin having 8 carboxyl groups, a methyl ester of porphyrin having 7 carboxyl groups, a methyl ester of porphyrin having 6 carboxyl groups, a methyl ester of porphyrin having 5 carboxyl groups and a methyl ester of porphyrin having 4 carboxyl groups in this sequence. Fractions of these were collected and concentrated under reduced pressure to give porphyrin solids. They were 370 mg of a methyl ester of porphyrin having 8 carboxyl groups, 78 mg of a methyl ester of porphyrin having 7 carboxyl groups, 20 mg of a methyl ester of porphyrin having 6 carboxyl groups, 18 mg of a methyl ester of porphyrin having 5 carboxyl groups, and 210 mg of a methyl ester of porphyrin having 4 carboxyl groups which were recovered at a ratio of 100, 98, 100, 90, and 95%, respectively.

What we claim is:

1. A process for separatig porphyrins, which comprises
   (1) adjusting the pH of the liquid phase of a culture broth containing at least two porphyrins to about 2.5 to about 4 and collecting the resulting solid containing the porphyrins,
   (2) either (a) preparing an acidic aqueous solution of said solid and adjusting the pH of its liquid phase left after removal of insoluble matter to about 6 to about 8 to form an aqueous solution containing the porphyrins, or (b) preparing an acid-containing lower alcohol solution of said solid, adjusting the pH of its liquid phase left after removal of insoluble matter, adding water in an amount at least twice the amount of the solution to precipitate lower alkyl esters of the porphyrins, collecting the precipitates and dissolving them in an organic solvent to form an organic solvent solution of the porphyrin esters,
   (3) contacting the solution obtained in (a) or (b) in step (2) with a copolymer having a surface area of at least about 700 m²/g and derived from
      (i) divinylbenzene,
      (ii) styrene or its functional derivative,
      (iii) an alkenyl ester of a benzenepolycarboxylic acid represented by the following formula

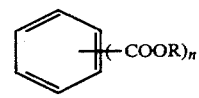

wherein R represents an alkenyl group having 3 to 10 carbon atoms, and n is 2 or 3, thereby permitting adsorption of the porphyrins or their esters to the copolymer, and
   (4) thereafter, eluting the copolymer to obtain fractions of the individual porphyrins or their esters.

2. The process of claim 1 wherein the porphyrins contained in the culture broth are a mixture of at least two porphyrins in free acid form having 4, 5, 6, 7 and 8 carboxyl groups.

3. The process of claim 1 wherein the culture broth is obtained by cultivating a porphyrin-producing microorganism belonging to the genus Arthrobacter.

4. The process of claim 3 wherein the porphyrin-producing microorganism is a strain selected from the group consisting of *Arthrobacter hyalinus, Arthrobacter pascens,* and mutants and variants of these microorganisms.

5. The process of claim 1 wherein the solution (a) is contacted in step (3), and the elution in step (4) is carried out by using an aqueous solution of a lower alcohol as an eluent.

6. The process of claim 1 wherein the solution (b) is contacted in step (3), and the elution in step (4) is carried out by using a mixture of a lower alcohol and a chlorine-containing solvent as an eluent.

7. The process of claim 1 wherein the amount of the component (ii) of the copolymer is about 30 to about 80% by weight based on the total amount of the components (i) and (ii), and the amount of the component (iii) is about 0.1 to about 30% by weight based on the total amount of the components (i), (ii) and (iii).

* * * * *